(12) United States Patent
Essex et al.

(10) Patent No.: US 8,099,250 B2
(45) Date of Patent: Jan. 17, 2012

(54) IMPEDANCE PARAMETER VALUES

(75) Inventors: Tim Essex, Clayfield (AU); Leigh Cordwin Ward, Kenmore Hills (AU)

(73) Assignee: Impedimed Limited, Eight Mile Plains, Queensland (AU)

( * ) Notice: Subject to any disclaimer, the term of this patent is extended or adjusted under 35 U.S.C. 154(b) by 262 days.

(21) Appl. No.: 11/997,468

(22) PCT Filed: Jul. 27, 2006

(86) PCT No.: PCT/AU2006/001057
§ 371 (c)(1),
(2), (4) Date: Jul. 15, 2008

(87) PCT Pub. No.: WO2007/014417
PCT Pub. Date: Feb. 8, 2007

(65) Prior Publication Data
US 2008/0270051 A1    Oct. 30, 2008

(30) Foreign Application Priority Data

Aug. 2, 2005 (AU) ................................ 2005904125

(51) Int. Cl.
*G01R 27/00* (2006.01)
(52) U.S. Cl. .............................. 702/65; 702/75; 702/189
(58) Field of Classification Search .................... 702/65, 702/75, 189; 324/649, 650; 315/5.27, 5.28, 315/5.39; 314/7; 73/335.03
See application file for complete search history.

(56) References Cited

U.S. PATENT DOCUMENTS

| | | |
|---|---|---|
| 3,316,896 A | 5/1967 | Thomasset |
| 3,851,641 A | 12/1974 | Toole et al. |
| 3,871,359 A | 3/1975 | Pacela |
| 4,008,712 A | 2/1977 | Nyboer |
| 4,034,854 A | 7/1977 | Bevilacqua |
| 4,144,878 A | 3/1979 | Wheeler |
| 4,184,486 A | 1/1980 | Papa |
| 4,291,708 A | 9/1981 | Frei et al. |
| 4,314,563 A | 2/1982 | Wheeler |
| 4,365,634 A | 12/1982 | Bare et al. |

(Continued)

FOREIGN PATENT DOCUMENTS

CA     2231038      11/1999

(Continued)

OTHER PUBLICATIONS

International Search Report and Written Opinion cited in PCT/AU2006/001057 (5 pages).

(Continued)

*Primary Examiner* — Mohamed Charioui
*Assistant Examiner* — Elias Desta
(74) *Attorney, Agent, or Firm* — Knobbe, Martens, Olson & Bear, LLP

(57) ABSTRACT

A method of determining parameter values used in impedance analysis of a subject. The method includes using a processing system to determine a number of impedance measurements at a corresponding number of frequencies. The impedance measurements are used to determine estimates of parameter values, with the estimates being used to determine theoretical impedance values based on the parameter value estimates. The theoretical impedance values are compared to the measured impedance values to allow a modification direction to be determined for at least one of the parameter value estimates. This is then used to modify at least one parameter value estimate, with the parameter values being determined at least in part from one or more modified parameter value estimates.

27 Claims, 10 Drawing Sheets

U.S. PATENT DOCUMENTS

| | | |
|---|---|---|
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,468,832 A | 9/1984 | Bai et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A * | 7/1986 | Cook ............................... 702/65 |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,895,163 A | 1/1990 | Libke et al. |
| 4,899,758 A * | 2/1990 | Finkelstein et al. .......... 600/485 |
| 4,905,705 A | 3/1990 | Kizakevich et al. |
| 4,911,175 A | 3/1990 | Shizgal |
| 4,942,880 A | 7/1990 | Slovak |
| 4,951,682 A | 8/1990 | Petre |
| 5,025,784 A | 6/1991 | Shao et al. |
| 5,063,937 A | 11/1991 | Ezenwa et al. |
| 5,143,079 A | 9/1992 | Frei et al. |
| 5,197,479 A | 3/1993 | Hubelbank et al. |
| 5,246,008 A | 9/1993 | Mueller |
| 5,280,429 A | 1/1994 | Withers |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel |
| 5,449,000 A | 9/1995 | Libke et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,544,662 A | 8/1996 | Saulnier et al. |
| 5,588,429 A | 12/1996 | Isaacson et al. |
| 5,704,355 A | 1/1998 | Bridges |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 6,011,992 A | 1/2000 | Hubbard et al. |
| 6,015,389 A | 1/2000 | Brown |
| 6,018,677 A | 1/2000 | Vidrine et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Ferrer et al. |
| 6,173,003 B1 | 1/2001 | Whikehart et al. |
| 6,228,022 B1 | 5/2001 | Friesem et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,497,659 B1 | 12/2002 | Rafert |
| 6,532,384 B1 | 3/2003 | Fukuda |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,625,487 B2 | 9/2003 | Herleikson |
| 6,631,292 B1 | 10/2003 | Liedtke |
| 6,633,777 B2 | 10/2003 | Szopinski |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Blunsden et al. |
| 6,724,200 B2 | 4/2004 | Fukuda |
| 6,760,617 B2 | 7/2004 | Ward et al. |
| 6,768,921 B2 | 7/2004 | Organ et al. |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 7,130,680 B2 | 10/2006 | Kodama et al. |
| 7,148,701 B2 | 12/2006 | Park et al. |
| 7,212,852 B2 | 5/2007 | Smith et a |
| 7,457,660 B2 | 11/2008 | Smith et al. |
| 7,477,937 B2 | 1/2009 | Iijima et al. |
| 7,706,872 B2 | 4/2010 | Min et al. |
| 7,733,224 B2 | 6/2010 | Tran |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2002/0020138 A1 | 2/2002 | Walker et al. |
| 2002/0022787 A1 | 2/2002 | Takehara et al. |
| 2002/0072686 A1 | 6/2002 | Hoey et al. |
| 2002/0079910 A1 | 6/2002 | Fukuda |
| 2002/0093991 A1 | 7/2002 | Kurihara et al. |
| 2002/0093992 A1 | 7/2002 | Plangger |
| 2002/0123694 A1 | 9/2002 | Organ et al. |
| 2002/0161311 A1 | 10/2002 | Ward et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |
| 2003/0050570 A1 | 3/2003 | Kodama et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2004/0015095 A1 | 1/2004 | Li et al. |
| 2004/0019292 A1 | 1/2004 | Drinan et al. |
| 2004/0077944 A1 | 4/2004 | Steinberg et al. |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0252870 A1 | 12/2004 | Reeves et al. |
| 2005/0033281 A1 | 2/2005 | Bowman et al. |
| 2005/0039763 A1 | 2/2005 | Kraemer et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0203435 A1 | 9/2005 | Nakada |
| 2005/0261743 A1 | 11/2005 | Kroll |
| 2006/0004300 A1 | 1/2006 | Kennedy |
| 2006/0085048 A1 | 4/2006 | Cory et al. |
| 2006/0085049 A1 | 4/2006 | Cory et al. |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0224079 A1 | 10/2006 | Washchuk |
| 2006/0224080 A1 | 10/2006 | Oku et al. |
| 2006/0264775 A1 | 11/2006 | Mills et al. |
| 2006/0270942 A1 | 11/2006 | McAdams |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0087703 A1 | 4/2007 | Li et al. |
| 2007/0106342 A1 | 5/2007 | Schumann |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |

| | | | |
|---|---|---|---|
| 2008/0039700 | A1 | 2/2008 | Drinan et al. |
| 2008/0205717 | A1 | 8/2008 | Reeves et al. |
| 2008/0319336 | A1 | 12/2008 | Ward et al. |
| 2009/0043222 | A1 | 2/2009 | Chetham |
| 2009/0076343 | A1 | 3/2009 | James et al. |
| 2009/0076345 | A1 | 3/2009 | Manicka et al. |
| 2009/0076350 | A1 | 3/2009 | Bly et al. |
| 2009/0082679 | A1 | 3/2009 | Chetham |
| 2009/0105555 | A1 | 4/2009 | Dacso et al. |
| 2009/0143663 | A1 | 6/2009 | Chetham |
| 2009/0177099 | A1 | 7/2009 | Smith et al. |
| 2009/0287102 | A1 | 11/2009 | Ward |
| 2009/0318778 | A1 | 12/2009 | Dacso et al. |
| 2010/0168530 | A1 | 7/2010 | Chetham et al. |

FOREIGN PATENT DOCUMENTS

| | | |
|---|---|---|
| CA | 2613524 | 1/2007 |
| CA | 2615845 | 1/2007 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 339471 | 3/1997 |
| EP | 865763 | 9/1998 |
| EP | 0869360 | 10/1998 |
| EP | 1112715 | 4/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1338246 | 8/2003 |
| EP | 1452131 | 9/2004 |
| EP | 1553871 | 7/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| FR | 2486386 | 1/1982 |
| FR | 2748928 | 11/1997 |
| GB | 2131558 | 6/1984 |
| GB | 2260416 | 4/1993 |
| GB | 2426824 | 12/2006 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 10-225521 | 8/1998 |
| JP | 11070090 | 3/1999 |
| JP | 2000107138 | 4/2000 |
| JP | 2000139867 | 5/2000 |
| JP | 2001321352 | 11/2001 |
| JP | 2002330938 | 11/2002 |
| JP | 2003116805 | 4/2003 |
| JP | 2008022995 | 7/2008 |
| RU | 2112416 | 6/1998 |
| WO | WO 88/07392 | 10/1988 |
| WO | WO 93/18821 | 9/1993 |
| WO | WO 96/01586 | 1/1996 |
| WO | WO 96/12439 | 5/1996 |
| WO | WO 96/32652 | 10/1996 |
| WO | WO 97/11638 | 4/1997 |
| WO | WO 97/14358 | 4/1997 |
| WO | WO 98/06328 | 2/1998 |
| WO | WO 98/23204 | 6/1998 |
| WO | WO 98/33553 | 8/1998 |
| WO | WO 00/40955 | 7/2000 |
| WO | WO 00/79255 | 12/2000 |
| WO | WO 01/50954 | 7/2001 |
| WO | WO 01/67098 | 9/2001 |
| WO | WO 02/062214 | 8/2002 |
| WO | WO 02/094096 | 11/2002 |
| WO | WO 2004/000115 | 12/2003 |
| WO | WO 2004/026136 | 4/2004 |
| WO | WO 2004/047635 | 6/2004 |
| WO | WO 2004/047638 | 6/2004 |
| WO | WO 2004/049936 | 6/2004 |
| WO | WO 2004/083804 | 9/2004 |
| WO | WO 2005/010640 | 2/2005 |
| WO | WO 2005/027717 | 3/2005 |
| WO | WO 2005/051194 | 6/2005 |
| WO | WO 2005/122888 | 12/2005 |
| WO | WO 2006/129108 | 12/2006 |
| WO | WO 2006/129116 | 12/2006 |
| WO | WO 2007/002991 | 1/2007 |
| WO | WO 2007/002992 | 1/2007 |
| WO | WO 2007/002993 | 1/2007 |
| WO | WO 2007/009183 | 1/2007 |
| WO | WO 2007/041783 | 4/2007 |
| WO | WO 2008/064426 | 6/2008 |
| WO | WO 2008/138062 | 11/2008 |
| WO | WO 2009/036369 | 3/2009 |
| WO | WO 2009/100491 | 8/2009 |
| WO | WO 2011/022068 | 2/2011 |
| WO | WO 2011/050393 | 5/2011 |
| WO | WO 2011/075769 | 6/2011 |

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

Al-Hatib, F.; Patient Instrument connection errors in bioelectrical impedance measurement; Physiological Measurement; vol. 19, No. 2, pp. 285-296; May 2, 1998.

Boulier, A. et al.; Fat-Free Mass Estimation By Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Bioelectrical impedance for monitoring the efficacy of lymphoedema treatment programmes; Breast Cancer Research and Treatment; vol. 38, pp. 169-176; 1996.

Cornish, B.H. et al.; Data analysis in multiple-frequency bioelectrical impedance analysis; Physiological Measurement; vol. 19, No. 2, pp. 275-283; May 1, 1998.

Cornish, B.H. et al.; Early diagnosis of lymphedema using multiple frequency bioimpedance; Lymphology; vol. 34, pp. 2-11; Mar. 2001.

Cornish, B.H. et al.; Early diagnosis of lymphoedema in postsurgery breast cancer patients; Annals New York Academy of Sciences; pp. 571-575; May 2000.

Cornish, B.H. et al.; Quantification of Lymphoedema using Multi-frequency Bioimpedance; Applied Radiation and Isotopes; vol. 49, Nos. 5/6, pp. 651-652; 1998.

De Luca, F. et al., Use of low-frequency electrical impedance measurements to determine phospholipid content in amniotic fluid; Physics in Medicine and Biology, vol. 41, pp. 1863-1869, 1996.

Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.

Dines K.A. et al.; Analysis of electrical conductivity imaging; Geophysics; vol. 46, No. 7, pp. 1025-1036; Jul. 1981.

Ellis, K.J. et al; Human hydrometry: comparison of multifrequency bioelectrical impedance with 2H2O and bromine dilution; Journal of Applied Physiology; vol. 85, No. 3, pp. 1056-1062; 1998.

Forslund, A.H. et al.; Evaluation of modified multicompartment models to calculate body composition in healthy males; American Journal of Clinical Nutrition; vol. 63, pp. 856-62; 1996.

Gersing, E.; Impedance spectroscopy on living tissue for determination of the state of Organs; Bioelectrochemistry and Bioenergetics; vol. 45, pp. 145-149; 1998.

Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. At Chapel Hill; pp. 446-453; Jun. 1990.

Gudivaka R. et al; Single- and multifrequency models for bioelectrical impedance analysis of body water compartments; Applied Physiology; vol. 87, Issue 3, pp. 1087-1096; 1999.

Jones, C.H. et al; Extracellular fluid volume determined by bioelectric impedance and serum albumin in CAPD patients; Nephrology Dialysis Transplantation; vol. 13, pp. 393-397; 1998.

Jossinet, J. et al.; A Study For Breast Imaging with a Circular Array of Impedance Electrodes; Proc. Vth Int. Conf. Bioelectrical Impedance, 1981, Tokyo, Japan; pp. 83-86; 1981.

Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.

Kanai, H. et al.; Electrical Measurement of Fluid Distribution in Legs and Arms; Medical Progress through technology; pp. 159-170; 1987.

Kim, C.T. et al.; Bioelectrical impedance changes in regional extracellular fluid alterations; Electromyography and Clinical Neurophysiology; vol. 37, pp. 297-304; 1997.

Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; Sep. 1-4, 2005.

Lozano, A. et al.; Two-frequency impedance plethysmograph: real and imaginary parts; Medical & Biological Engineering & Computing; vol. 28, No. 1, pp. 38-42; Jan. 1990.

Lukaski, H.C. et al.; Estimation of Body Fluid Volumes Using Tetrapolar Bioelectrical Impedance Measurements; Aviation, Space, and Environmental Medicine; pp. 1163-1169; Dec. 1998.

Man, B. et al. Results of Preclinical Tests for Breast Cancer Detection by Dielectric Measurements; XII Int. Conf. Med. Engng. 1979, Jerusalem, Israel. Springer Int., Berlin; Section 30.4; 1980.

Mattar, J.A., Application of Total Body Impedance to the Critically III Patient, New Horizons, vol. 4, No. 4, pp. 493-503, 1996.

McDougal D., et al.; Body Composition Measurements From Whole Body Resistance and Reactance; Surgical Forum; vol. 36, pp. 43-44; 1986.

Osterman K.S. et al.; Multifrequency electrical impedance imaging: preliminary in vivo experience in breast; Physiological Measurement; vol. 21, No. 1, pp. 99-109; Feb. 2000.

Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.

Pethig, R. et al.; The Passive Electrical Properties of Biological Systems: Their Significance in Physiology, Biophysics and Biotechnology; Physics in Medicine and Biology; vol. 32, pp. 933-970; 1987.

Piperno, G. et al.; Breast Cancer Screening by Impedance Measurements; Frontiers of Medical & Biological Engineering; vol. 2, pp. 111-117; 1990.

Rigaud, B. et al.; Bioelectrical Impedance Techniques in Medicine; Critical Reviews in Biomedical Engineering; vol. 24 (4-6), pp. 257-351; 1996.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.

Skidmore, R. et al.; A Data Collection System for Gathering Electrical Impedance Measurements from the Human Breast; Clinical Physics Physiological Measurement; vol. 8, pp. 99-102; 1987.

Sollish, B.D. et al.; Microprocessor-assisted Screening Techniques; Israel Journal of Medical Sciences; vol. 17, pp. 859-864; 1981.

Steijaert, M. et al.; The use of multi-frequency impedance to determine total body water and extracellular water in obese and lean female individuals; International Journal of Obesity; vol. 21, pp. 930-934; 1997.

Surowiec, A.J. et al.; Dielectric Properties of Brest Carcinoma and the Surrounding Tissues; IEEE Transactions on Biomedical Engineering; vol. 35, pp. 257-263; 1988.

Tedner, B.; Equipment Using Impedance Technique for Automatic Recording of Fluid-Volume Changes During Haemodialysis; Medical & Biological Engineering & Computing; pp. 285-290; 1983.

Thomas. B.J. et al.; Bioelectrical impedance analysis for measurement of body fluid volumes—A review; Journal of Clinical Engineering; vol. 17, No. 16, pp. 505-510; 1992.

Thomas. B.J. et al.; Bioimpedance Spectrometry in Determination of Body Water Compartments: Accuracy and Clinical Significance; Applied Radiation and Isotopes; vol. 49, Nos. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in post-mastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Bella, et al., Relations Of Left Ventricular Mass To Fat-Free And Adipose Body Mass: The Strong Heart Study, (1998) Circulation, vol. 98, pp. 2538-2544.

Iacobellis, G., et al. Influence Of Excess Fat On Cardiac Morphology And Function: Study In Uncomplicated Obesity, (2002) Obesity Research, vol. 10, pp. 767-773.

Karason, K., et al., Impact Of Blood Pressure And Insulin On The Relationship Between Body Fat And Left Ventricular Structure, (2003) European Heart Journal, vol. 24, pp. 1500-1505.

Yoshinaga, M., Effect Of Total Adipose Weight And Systemic Hypertension On Left Ventricular Mass In Children, American Journal of Cardiology, (1995) vol. 76, pp. 785-787.

* cited by examiner

IMPEDANCE PARAMETER VALUES

BACKGROUND OF THE INVENTION

The present invention relates to a method and apparatus for determining parameter values used in impedance analysis of a subject.

DESCRIPTION OF THE PRIOR ART

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

One existing technique for determining biological parameters relating to a subject, such as cardiac function, or oedema, involves the use of bioelectrical impedance. This involves measuring the electrical impedance of a subject's body using a series of electrodes placed on the skin surface. Changes or values of electrical impedance can then used to determine parameters, such as changes in fluid levels, which can in turn be used as indicators of attributes of cardiac cycle or oedema.

Complex signal processing is required to ensure measurements can be interpreted. An example of this is described in International patent publication no WO2004/032738, in which the responsiveness of a patient to an applied current is measured to determine a number of impedance values. The measured impedance values are plotted as a frequency dependent locus, which is then extrapolated to determine impedance values at zero and infinite applied frequencies.

However, such plotting and extrapolation techniques are computationally expensive, making it difficult to analyse impedance measurements in real time, or within portable devices that have limited computational power.

SUMMARY OF CERTAIN INVENTIVE ASPECTS

In a first broad form the present invention provides a method of determining parameter values used in impedance analysis of a subject, the method including, in a processing system:
   a) determining a number of impedance measurements at a corresponding number of frequencies;
   b) determining estimates of the parameter values;
   c) determining theoretical impedance values based on the parameter value estimates;
   d) comparing the theoretical impedance values to the measured impedance values;
   e) determining at least one modification direction for at least one of the parameter value estimates in accordance with the results of the comparison; and,
   f) modifying at least one parameter value estimate in accordance with the determined direction, the parameter values being determined at least in part from one or more modified parameter value estimates.

Typically the method includes, in the computer system, iteratively modifying the parameter value estimates to thereby determine the parameter values.

Typically the method includes, in the processing system, comparing the theoretical impedance values to the measured impedance values:
   a) determining a theoretical impedance locus using the parameter value estimates;
   b) determining a measured impedance locus associated with each measured impedance; and,
   c) determining an intersection between each measured impedance locus and the theoretical impedance locus.

Typically the method includes, in the processing system:
   a) determining a point associated with each intersection;
   b) determining a linear regression based at least partially on the points; and,
   c) determining the modification direction based at least partially on at least one of:
      i) the relative position of the regression line and at least one of the points; and,
      ii) the gradient of the regression line.

Typically the method includes, in the computer system:
   a) determining a pair of chords associated with each point of intersection, the chords representing the distance to locations at which the theoretical impedance locus represents predetermined impedance values; and,
   b) determining a point associated with each pair of chords; and,
   c) determining the linear regression in accordance with the value of the points.

Typically the method includes, in the processing system:
   a) determining four impedance measurements, each impedance measurement being made at a respective frequency;
   b) comparing each measured impedance value to a corresponding theoretical impedance value;
   c) determining the modification direction based at least in part on the results of the comparison.

Typically the method includes, in the processing system:
   a) determining a point based on the comparison of each measured impedance value with a corresponding theoretical impedance value;
   b) determining a linear regression based at least partially on the points; and,
   c) determining the modification direction based at least partially on at least one of:
      i) the relative position of the regression line and at least one of the points; and,
      ii) the gradient of the regression line.

Typically the method includes, in the processing system:
   a) determining the relative position of the regression line and a predetermined point; and,
   b) determining the modification direction for modifying a predetermined one of the parameter value estimates using the relative position.

Typically the method based on the relative position of the regression line and at least one of the points.
   a) comparing the gradient of the regression line and a line based on at least one of the parameter value estimates; and,
   b) determining the modification direction for the at least one of the parameter value estimate using the results of the comparison.

Typically the method includes, in the processing system, at least one of:
   a) modifying an estimated value of $R_0$ using a point based on the impedance measured at a first frequency;
   b) modifying an estimated value of $R_\infty$ using a point based on the impedance measured at a second frequency; and,
   c) modifying an estimated value of $\alpha$ using a gradient of the regression line, where:
      $\alpha$ has a value between 0 and 1;
      $R_0$ is the theoretical impedance at zero applied angular frequency; and, $R_\infty$ is the theoretical impedance at infinite applied angular frequency.

Typically the method includes, in the processing system, estimating values for parameters $R_0$, $R_\infty$, and $\alpha$, where:
  $\alpha$ has a value between 0 and 1;
  $R_0$ is the theoretical impedance at zero applied angular frequency; and,
  $R_\infty$ is the theoretical impedance at infinite applied angular frequency.

Typically the method includes, in the processing system, determining the theoretical impedance using the equation:

$$Z = R_\infty + \frac{R_0 - R_\infty}{1 + (j\omega\tau)^\alpha} \text{ where:}$$

Z is the measured impedance at angular frequency $\omega$,
$R_0$ is the resistance at zero frequency,
$R_\infty$ is the resistance at infinite frequency,
$\tau$ is a time constant, and
$\alpha$ has a value between 0 and 1.

Typically the method includes, in the processing system, using the parameter values to determine at least one of:
  a) a ratio of extra- to intra-cellular fluid; and,
  b) an indication of the at least one of the presence, absence or degree of tissue oedema in the subject.

Typically the method includes, in the computer system:
  a) determining parameter values associated with first and second body segments;
  b) for each body segment, determining an index indicative of a ratio of the extra- to intra-cellular fluid;
  c) determining an index ratio based on the index for the first and second body segments;
  d) comparing the index ratio to at least one reference; and,
  e) determining the presence, absence or degree of tissue oedema based on the results of the comparison.

Typically the method includes, in the computer system, displaying an indication of at least one of:
  a) the parameter values;
  b) a ratio of extra- to intra-cellular fluid; and,
  c) an indication of the at least one of the presence, absence or degree of tissue oedema in the subject.

Typically the method includes, in the processing system, receiving the impedance measurements from a measuring device.

Typically the method includes, in the processing system:
  a) causing one or more electrical signals to be applied to the subject using a first set of electrodes, the one or more electrical signals having a plurality of frequencies;
  b) determining an indication of electrical signals measured across a second set of electrodes applied to the subject in response to the applied one or more signals;
  c) determining from the indication and the one or more applied signals, an instantaneous impedance value at each of the plurality of frequencies; and,
  d) determining the index using the instantaneous impedance values.

Typically the method includes, in the processing system:
  a) generating control signals, the control signals being used to apply one or more signals to the subject;
  b) receiving an indication of the one or more signals applied to the subject;
  c) receiving an indication of one or more signals measured across the subject; and,
  d) determining the impedance measurements using the received indications.

In a second broad form the present invention provides apparatus for determining parameter values used in impedance analysis of a subject, the apparatus including a processing system for:
  a) determining a number of impedance measurements at a corresponding number of frequencies;
  b) determining estimates of the parameter values;
  c) determining theoretical impedance values based on the parameter value estimates;
  d) comparing the theoretical impedance values to the measured impedance values;
  e) determining at least one modification direction for at least one of the parameter value estimates in accordance with the results of the comparison; and,
  f) modifying the at least one parameter value estimate in accordance with the determined direction.

Typically the apparatus includes:
  a) a current supply for generating an alternating current at each of the number of frequencies;
  b) at least two supply electrodes for applying the generated alternating current to a subject;
  c) at least two measurement electrodes for detecting a voltage across the subject; and,
  d) a sensor coupled to the measurement electrodes for determining the voltage, the sensor being coupled to the processing system to thereby allow the processing system to determine the measured impedance.

Typically the current supply generates the alternating current at each frequency by at least one of:
  a) superposing a number of signals to thereby generate an alternating at each frequency simultaneously; and,
  b) generating a number of alternating currents, each alternating current being at a respective frequency, in turn.

Typically the apparatus is for performing the method of the first broad form of the invention.

In a third broad form the present invention provides a method of diagnosing the presence, absence or degree of one or more conditions in a subject, the method including, in a processing system:
  a) determining a number of impedance measurements at a corresponding number of frequencies;
  b) determining estimates of the parameter values;
  c) determining theoretical impedance values based on the parameter value estimates;
  d) comparing the theoretical impedance values to the measured impedance values;
  e) determining at least one modification direction for at least one of the parameter value estimates in accordance with the results of the comparison;
  f) modifying at least one parameter value estimate in accordance with the determined direction, the parameter values being determined at least in part from one or more modified parameter value estimates; and,
  g) using the determined parameter values in diagnosing the presence, absence or degree of one or more conditions in the subject.

It will be appreciated that the broad forms of the invention may be used individually or in combination, and may be used for diagnosis of the presence, absence or degree of a range of conditions and illnesses, including, but not limited to oedema, pulmonary oedema, lymphodema, body composition, cardiac function, and the like.

BRIEF DESCRIPTION OF THE DRAWINGS

An example of the present invention will now be described with reference to the accompanying drawings, in which.

DETAILED DESCRIPTION OF CERTAIN INVENTIVE EMBODIMENTS

Figure 1:
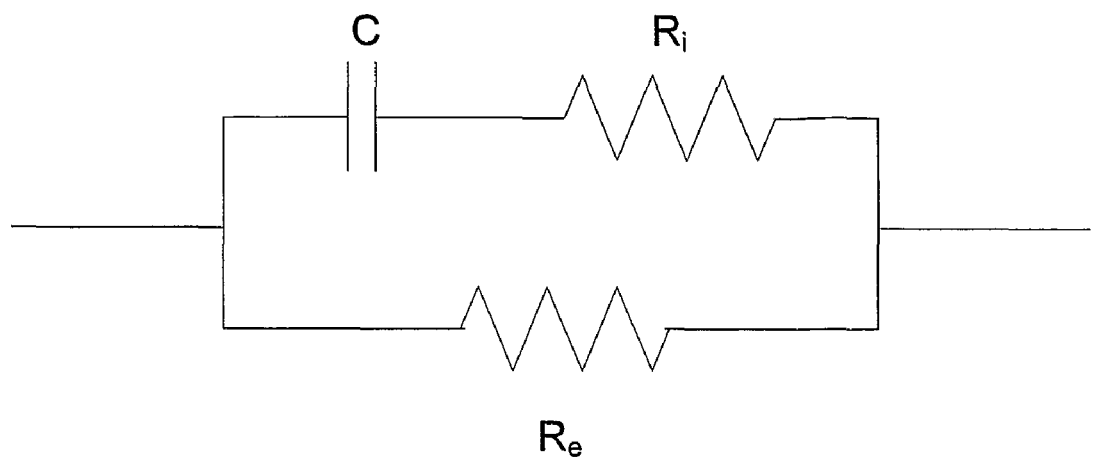
—FIG. 1 is a schematic of an example of a theoretical equivalent circuit for biological tissue.

FIG. 1 is an example of an equivalent circuit that effectively models the electrical behaviour of biological tissue. The equivalent circuit has two branches that represent current flow through extracellular fluid and intracellular fluid. The extracellular component of biological impedance is represented by $R_e$ and the intracellular component is represented by $R_i$. Capacitance of the cell membrane in the intracellular path is represented by C.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals $R_e$. At infinite frequency the capacitor acts as a perfect conductor and the current passes through the parallel resistive combination. The resistance at infinite frequency is given by $R_\infty = R_i R_e / (R_i + R_e)$.

Accordingly, the impedance of the equivalent circuit of FIG. 1 at an angular frequency ω, where ω=2π*frequency, is given by:

$$Z = R_\infty + \frac{R_0 - R_\infty}{1 + (j\omega\tau)} \quad (1)$$

where:
$R_\infty$=impedance at infinite applied frequency=$R_i R_e/(R_i + R_e)$,
$R_0$=impedance at zero applied frequency=$R_e$ and,
τ is the time constant of the capacitive circuit.

However, the above represents an idealised situation which does not take into account the fact that the cell membrane is an imperfect capacitor. The effect of this can be modelled through the use of an alternative equivalent circuit that incorporates a constant phase element, often represented as a frequency dependent resistor and capacitor in parallel. Such a circuit has been previously described in the literature, for example in S. Grimnes and O. G. Martinsen "Bioimpedance and Bioelectrical Basics", Academic Press London, 2000 and will not therefore be discussed in further detail. However, taking this into account leads to a modified model in which:

$$Z = R_\infty + \frac{R_0 - R_\infty}{1 + (j\omega\tau)^\alpha} \quad (2)$$

where α has a value between 0 and 1 and can be thought of as an indicator of the deviation of a real system from the ideal model.

It will be appreciated by persons skilled in the art that the following process can be performed in accordance with either of the above described models, but that the second model represented by equation (2) is preferably used as this more accurately reflects the impedance response of the subject.

Figure 2:
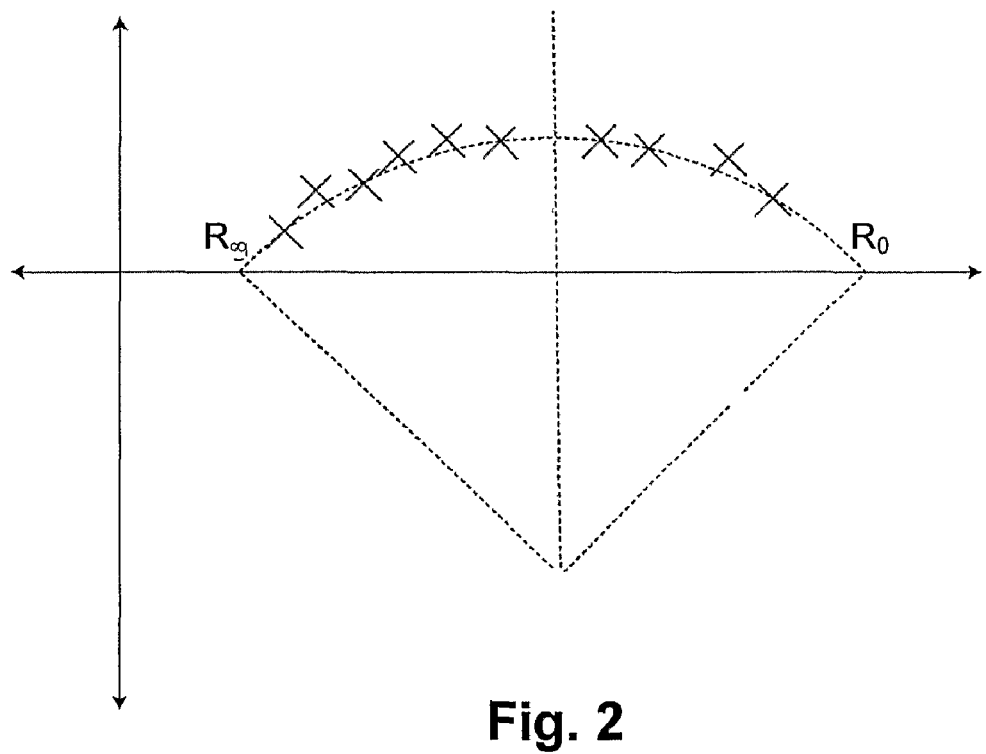
FIG. 2 is an example of a locus of impedance known as a "Wessel" plot.

As explained above, the prior art approach to determining the desired values of $R_0$ and $R_\infty$ has been to make impedance measurements at multiple frequencies and to construct a section of a "Wessel" (also known as a "Cole-Cole") plot. The plot can be extrapolated to determine $R_0$, $R_\infty$, as shown in FIG. 2.

Figure 3:
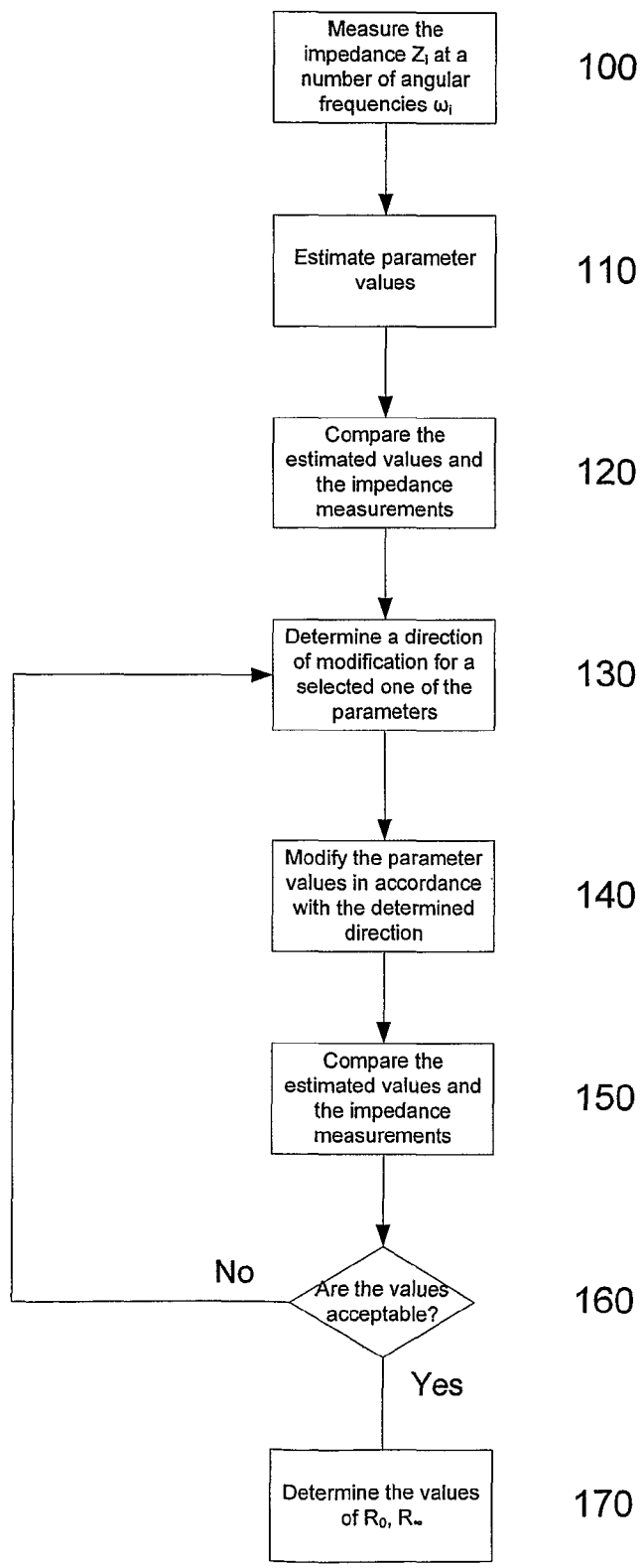
FIG. 3 is a flow chart of an overview of a process for determining parameters relating to impedance measurements.

An outline of one example for determining values of $R_0$ and $R_\infty$ for a given body segment will now be described with reference to FIG. 3.

In this example, at step 100, the impedance Z of a subject is measured at a number of different frequencies. At step 110, the measured impedances are used to provide initial estimates of parameter values, such as values for the parameters $R_0$, $R_\infty$, and α. This may be achieved using any one of a number of techniques as will be described in more detail below.

In any event, at step 120, a degree of correlation between the estimated values and the impedance measurements is determined, for example, by using the estimated values to calculate theoretical impedance values $Z_t$ for each of the measurement frequencies $\omega_i$, using equation (2). These values can then be compared to the measured values of impedance $Z_i$.

At step 130, the results of the comparison, and in particular, differences in the measured and theoretical impedances $Z_i$, $Z_t$ are used to determine a direction of modification for a selected one of the parameters. The parameter is modified in accordance with the determined direction, with the theoretical impedances $Z_t$ being recalculated at step 140.

The comparison is repeated at step 150, with an assessment of whether the estimated parameter values are acceptable at step 160. This will typically be achieved by determining if the difference between the calculated and measured impedance values fall within a predetermined ranges, which is typically established on the basis of the level of accuracy required in the final measurement.

In the event that the estimated values are not acceptable, the process returns to step 130, to determine a modification direction for either the same or a different one of the parameters.

This process is repeated until the estimated parameter values are deemed to be acceptable at step 160, at which point the estimated values of $R_0$ and $R_\infty$ can be used in determining parameters indicative of various body functions, such as oedema, fat-free mass, cardiac function, or the like.

Figure 4:
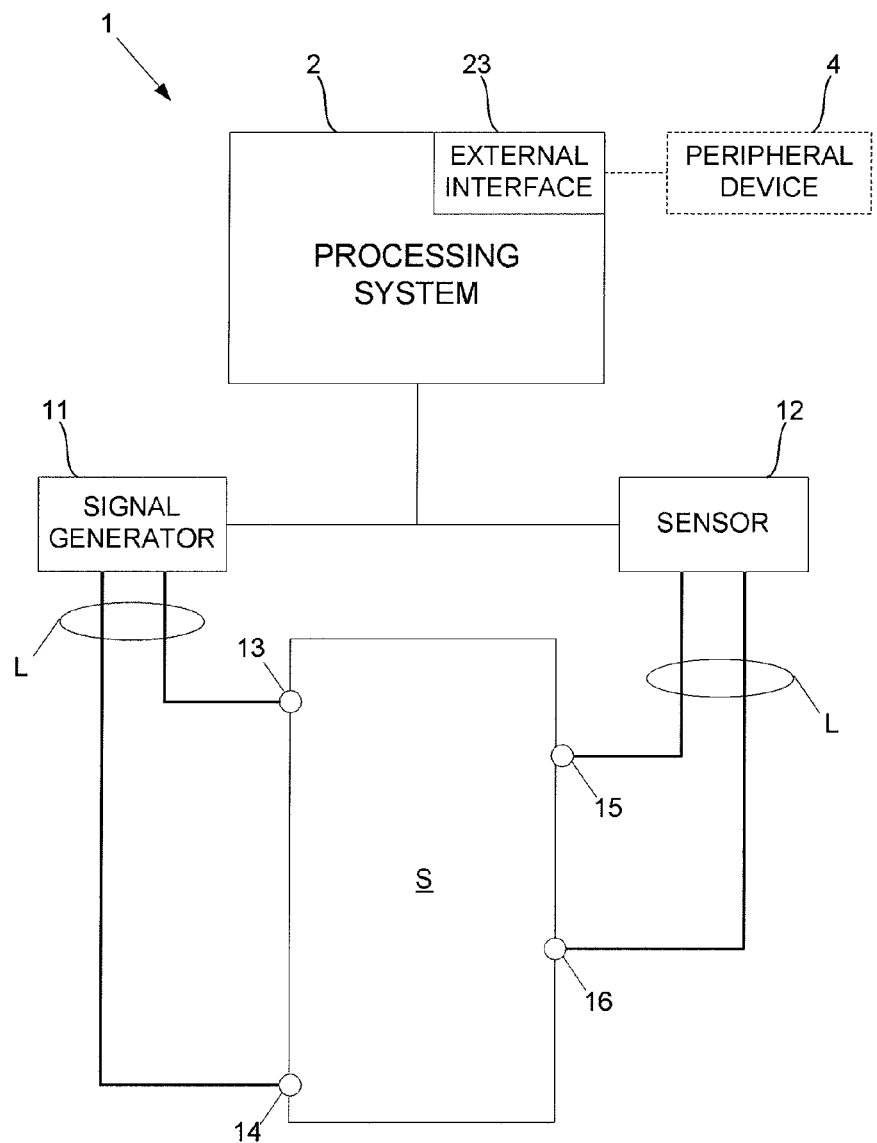
FIG. 4 is a schematic diagram of a first example of apparatus for monitoring bioimpedance.

An example of apparatus suitable for performing an analysis of a subject's impedance and determining impedance parameter values will now be described with reference to FIG. 4.

As shown the apparatus includes a measuring device 1 including a processing system 2 coupled to a signal generator 11 and a sensor 12. In use the signal generator 11 and the sensor 12 are coupled to respective electrodes 13, 14, 15, 16, provided on a subject S, via leads L, as shown. An optional external interface 23 can be used to couple the measuring device 1 to one or more peripheral devices 4, such as an external database, remote processing system or computer system, barcode scanner, or the like.

In use, the processing system 2 is adapted to generate control signals, which cause the signal generator 11 to generate one or more alternating signals, such as voltage or current signals, which can be applied to a subject S, via the electrodes 13, 14. The sensor 12 then determines the voltage across or current through the subject S using the electrodes 15, 16 and transfers appropriate signals to the processing system 2.

Accordingly, it will be appreciated that the processing system 2 may be any form of processing system which is suitable for generating appropriate control signals and interpreting an indication of measured signals to thereby determine the subject's bioelectrical impedance, and optionally determine other information such as cardiac parameters, or the presence absence or degree of pulmonary oedema.

The processing system 2 may therefore be a suitably programmed computer system, such as a laptop, desktop, PDA, smart phone or the like. Alternatively the processing system 2 may be formed from specialised hardware. Similarly, the I/O device may be of any suitable form such as a touch screen, a keypad and display, or the like.

It will be appreciated that the processing system 2, the signal generator 11 and the sensor 12 may be integrated into a common housing and therefore form an integrated device. Alternatively, the processing system 2 may be connected to the signal generator 11 and the sensor 12 via wired or wireless connections. This allows the processing system 2 to be provided remotely to the signal generator 11 and the sensor 12. Thus, the signal generator 11 and the sensor 12 may be provided in a unit near, or worn by the subject S, whilst the processing system 12 is situated remotely to the subject S.

In one example, the outer pair of electrodes 13, 14 are placed on the thoracic and neck region of the subject S. However, this depends on the nature of the analysis being performed. Thus, for example, whilst this electrode arrangement is suitable for cardiac function analysis, in lymphoedema, the electrodes would typically be positioned on the limbs, as required.

Once the electrodes are positioned, an alternating signal is applied to the subject S. This may be performed either by applying an alternating signal at a plurality of frequencies simultaneously, or by applying a number of alternating signals at different frequencies sequentially. The frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between an inner pair of electrodes 15, 16. The acquired signal and the measured signal will be a superposition of potentials generated by the human body, such as the ECG, and potentials generated by the applied current.

Optionally the distance between the inner pair of electrodes may be measured and recorded. Similarly, other parameters relating to the subject may be recorded, such as the height, weight, age, sex, health status, any interventions and the date and time on which they occurred. Other information, such as current medication, may also be recorded.

To assist accurate measurement of the impedance, buffer circuits may be placed in connectors that are used to connect the voltage sensing electrodes 15, 16 to the leads L. This ensures accurate sensing of the voltage response of the subject S, and in particular helps eliminate contributions to the measured voltage due to the response of the leads L, and reduces signal loss.

This in turn greatly reduces artefacts caused by movement of the leads L, which is particularly important during dialysis as sessions usually last for several hours and the subject will move around and change positions during this time.

A further option is for the voltage to be measured differentially, meaning that the sensor used to measure the potential at each electrode 15 only needs to measure half of the potential as compared to a single ended system.

The current measurement system may also have buffers placed in the connectors between the electrodes 13, 14 and the leads L. In one example, current can also be driven or sourced through the subject S symmetrically, which again greatly reduced the parasitic capacitances by halving the common-mode current. Another particular advantage of using a symmetrical system is that the micro-electronics built into the connectors for each electrode 13, 14 also removes parasitic capacitances that arise when the subject S, and hence the leads L move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 5:
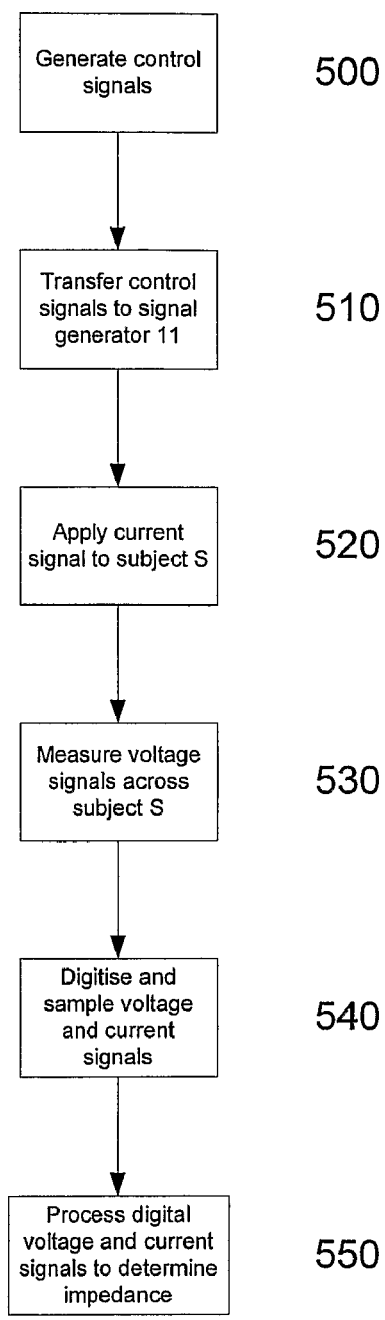
FIG. 5 is a flowchart of an example of a process for performing impedance determination.

An example of the operation of the apparatus for performing bioimpedance analysis will now be described with reference to FIG. 5.

At step 500, the processing system 2 operates to generate control signals which are provided to the signal generator 11 at step 510, thereby causing the signal generator to apply an alternating current signal to the subject S, at step 520. Typically the signal is applied at each of a number of frequencies $f_i$ to allow multiple frequency analysis to be performed.

At step 530 the sensor 12 senses voltage signals across the subject S. At step 540 the measuring device, operates to digitise and sample the voltage and current signals across the subject S, allowing these to be used to determine instantaneous bioimpedance values for the subject S at step5.

Figure 6:
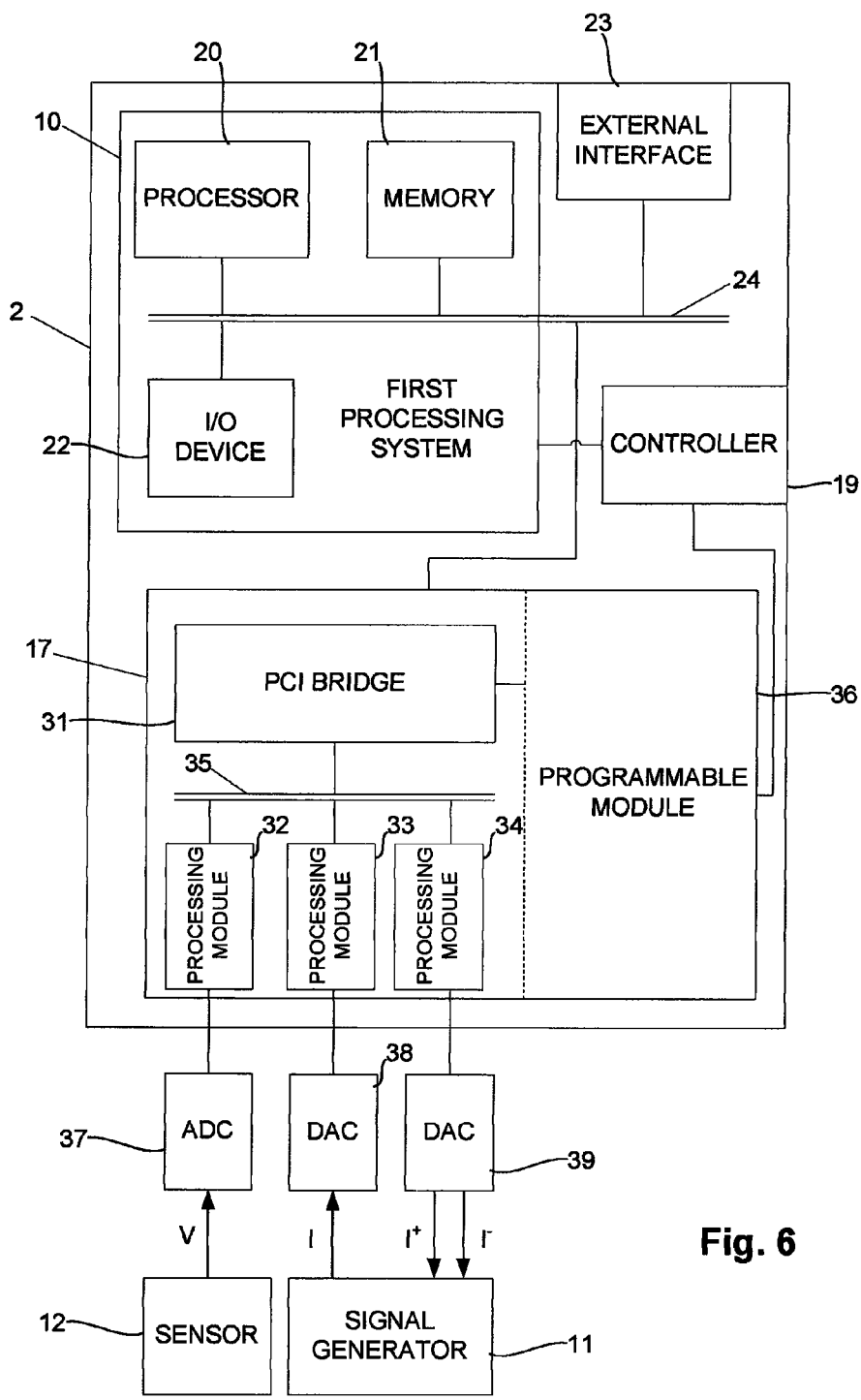
FIG. 6 is a schematic diagram of a second example of apparatus for monitoring bioimpedance.
Figure 7A:
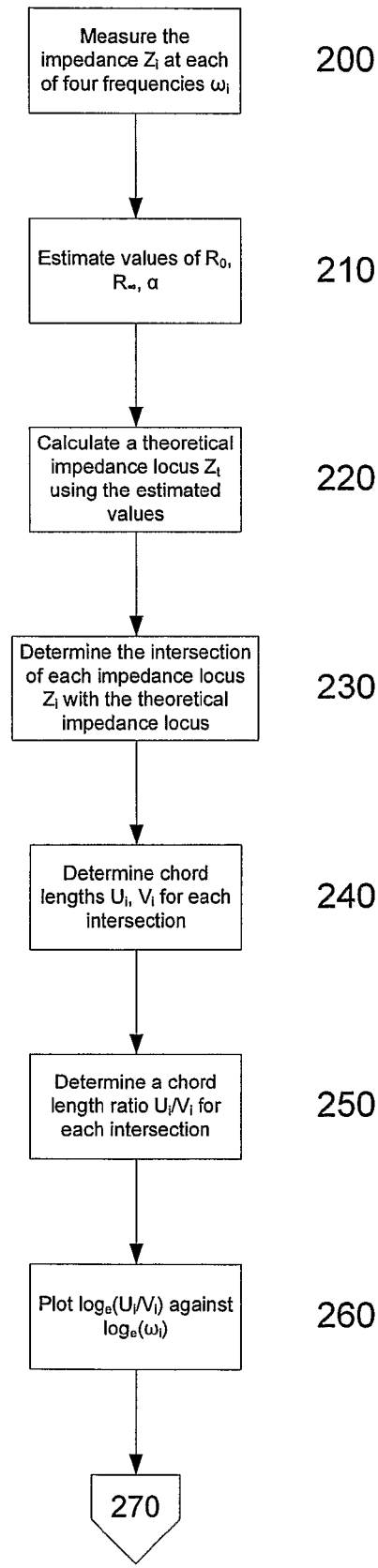
FIGS. 7A to 7C are a flow chart of an example of the process for determining parameters relating to impedance measurements.
Figure 7B:
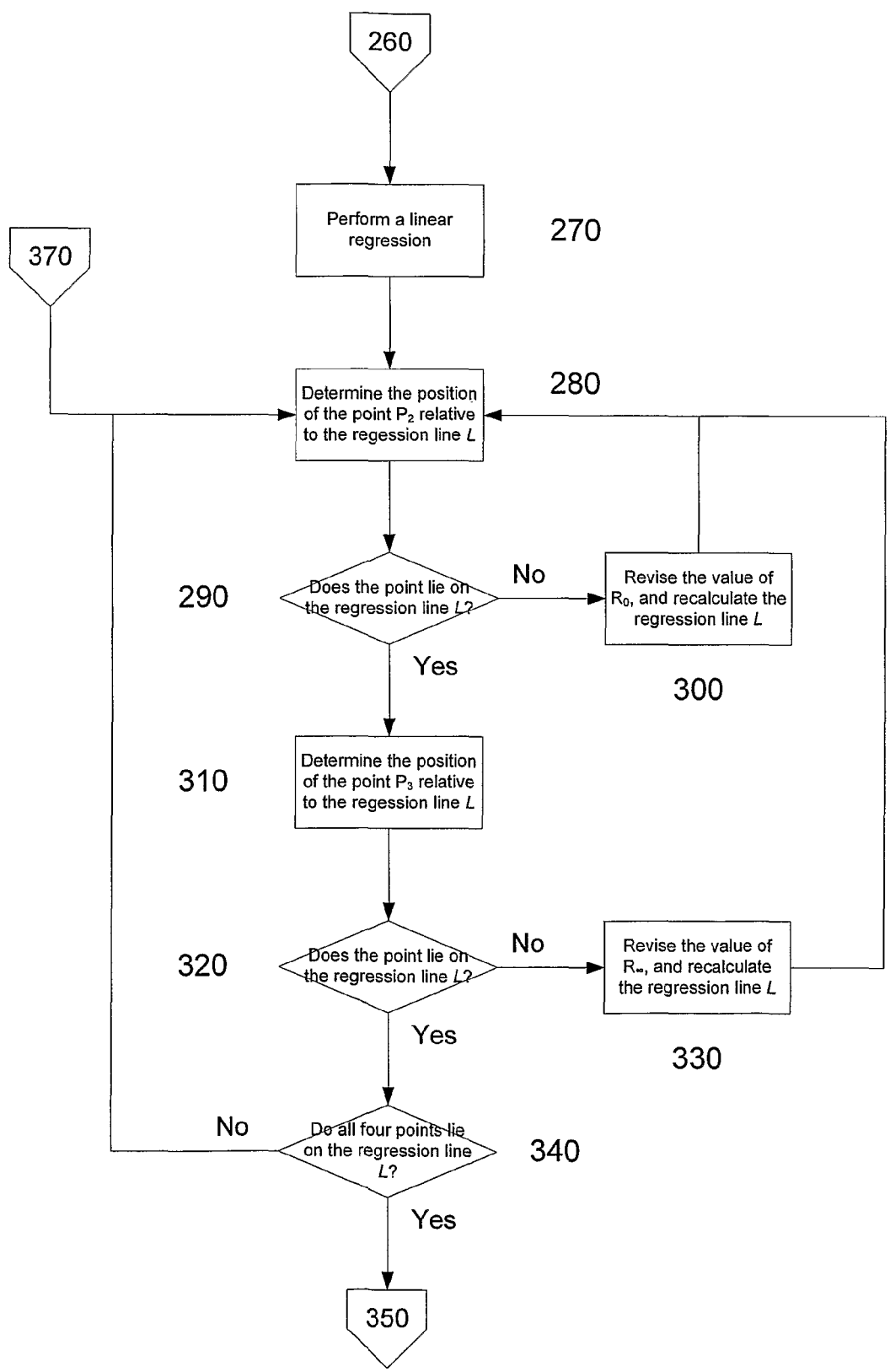
Figure 7C:
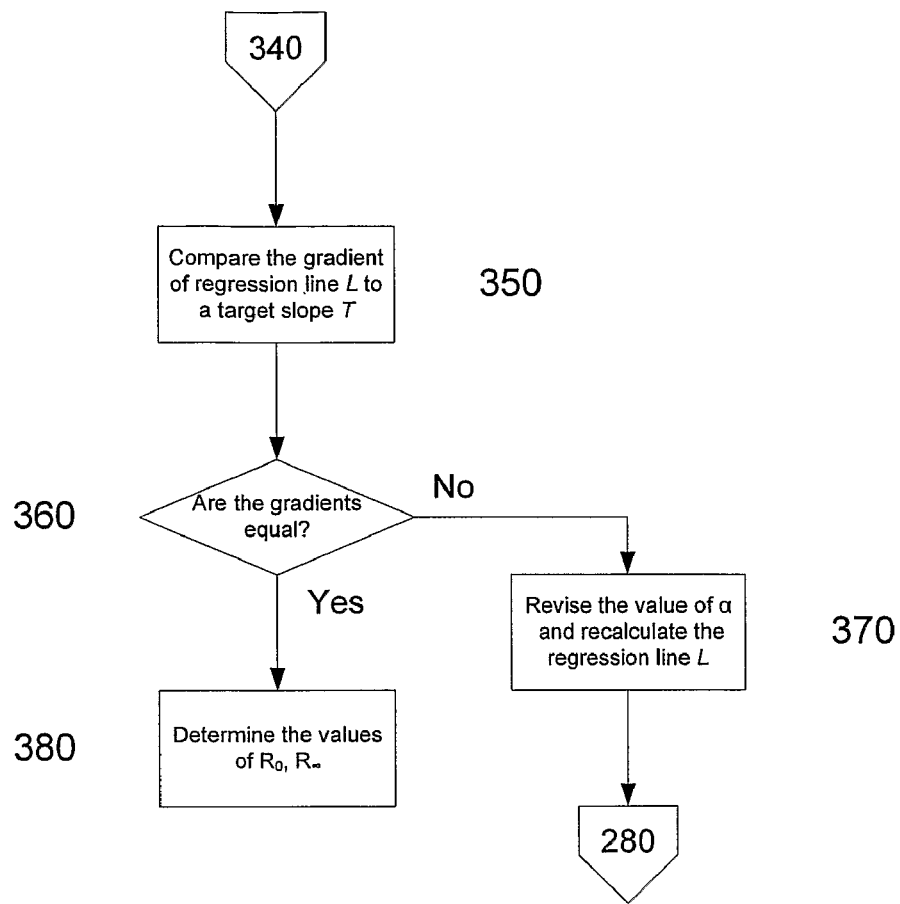

A specific example of the apparatus will now be described in more detail with respect to FIG. 6.

In this example, the processing system 2 includes a first processing system 10 having a processor 20, a memory 21, an input/output (I/O) device 22, and an external interface 23, coupled together via a bus 24. The processing system 2 also includes a second processing system 17, in the form of a processing module. A controller 19, such as a micrologic controller, may also be provided to control activation of the first and second processing systems 10, 17.

In use, the first processing system 10 controls the operation of the second processing system 17 to allow different impedance measurement procedures to be implemented, whilst the second processing system 17 performs specific processing tasks, to thereby reduce processing requirements on the first processing system 10.

Thus, the generation of the control signals, as well as the processing to determine instantaneous impedance values is performed by the second processing system 17, which may therefore be formed from custom hardware, or the like. In one particular example, the second processing system 17 is formed from a Field Programmable Gate Array (FPGA), although any suitable processing module, such as a magnetologic module, may be used.

The operation of the first and second processing systems 10, 17, and the controller 19 is typically controlled using one or more sets of appropriate instructions. These could be in any suitable form, and may therefore include, software, firmware, embedded systems, or the like.

The controller 19 typically operates to detect activation of the measuring device through the use of an on/off switch (not shown). Once the controller detects device activation, the controller 19 executes predefined instructions, which in turn causes activation of the first and second processing systems 10, 17, including controlling the supply of power to the processing systems as required.

The first processing system 10 can then operate to control the instructions, such as the firmware, implemented by the second processing system 17, which in turn alters the operation of the second processing system 17. Additionally, the first processing system 10 can operate to analyse impedance determined by the second processing system 17, to allow biological parameters to be determined. Accordingly, the first processing system 10 may be formed from custom hardware or the like, executing appropriate applications software to allow the processes described in more detail below to be implemented.

It will be appreciated that this division of processing between the first processing system 10, and the second processing system 17, is not essential, but there are a number of benefits that will become apparent from the remaining description.

In this example, the second processing system 17 includes a PCI bridge 31 coupled to programmable module 36 and a bus 35, as shown. The bus 35 is in turn coupled to processing modules 32, 33, 34, which interface with ADCs (Analogue to Digital Converters) 37, 38, and a DAC (Digital to Analogue Converter) 39, respectively.

The programmable module 36 is formed from programmable hardware, the operation of which is controlled using the instructions, which are typically downloaded from the first processing system 10. The firmware that specifies the configuration of hardware 36 may reside in flash memory (not shown), in the memory 21, or may be downloaded from an external source via the external interface 23.

Alternatively, the instructions may be stored within inbuilt memory on the second processing system 17. In this example, the first processing system 10 typically selects firmware for implementation, before causing this to be implemented by the second processing system 17. This may be achieved to allow selective activation of functions encoded within the firmware, and can be performed for example using configuration data, such as a configuration file, or instructions representing applications software or firmware, or the like, as will be described in more detail below.

In either case, this allows the first processing system 10 to be used to control operation of the second processing system 17 to allow predetermined current sequences to be applied to the subject S. Thus, for example, different firmware would be utilised if the current signal is to be used to analyse the impedance at a number of frequencies simultaneously, for example, by using a current signal formed from a number of superposed frequencies, as compared to the use of current signals applied at different frequencies sequentially.

This allows a range of different current sequences to be applied to the subject by making an appropriate measurement type selection. Once this has been performed, the FPGA operates to generate a sequence of appropriate control signals I+, I−, which are applied to the subject S. The voltage induced across the subject being sensed using the sensor 12, allowing the impedance values to be determined and analysed by the second processing system 17.

Using the second processing system 17 allows the majority of processing to be performed using custom configured hardware. This has a number of benefits.

Firstly, the use of a second processing system 17 allows the custom hardware configuration to be adapted through the use of appropriate firmware. This in turn allows a single measuring device to be used to perform a range of different types of analysis.

Secondly, this vastly reduces the processing requirements on the first processing system 10. This in turn allows the first processing system 10 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of pulmonary oedema.

Thirdly, this allows the measuring device 1 to be updated. Thus for example, if an improved analysis algorithm is created, or an improved current sequence determined for a specific impedance measurement type, the measuring device can be updated by downloading new firmware via flash memory (not shown) or the external interface 23.

It will be appreciated that in the above examples, the processing is performed partially by the second processing system 17, and partially by the first processing system 10. However, it is also possible for processing to be performed by a single element, such as an FPGA, or a more generalised processing system.

As the FPGA is a customisable processing system, it tends to be more efficient in operation than a more generic processing system. As a result, if an FPGA alone is used, it is generally possible to use a reduced overall amount of processing, allowing for a reduction in power consumption and size. However, the degree of flexibility, and in particular, the range of processing and analysis of the impedance which can be performed is limited.

Conversely, if only a generic processing system is used, the flexibility is enhanced at the expensive of a decrease in efficiency, and a consequent increase in size and power consumption.

An example of the process for analysing impedance measurements utilising the apparatus of FIG. 4 or 6, will now be described with reference to FIGS. 7A to 7C, and 8A to 8C.

In particular, at step 200 the process involves measuring the impedance $Z_i$ at each of at least four angular frequencies $\omega_i$. At step 210, values of $R_0$, $R_\infty$ and $\alpha$ are estimated and then used to calculate a theoretical impedance locus $Z_t$, based on the estimated values and using equation (2) above, at step 220.

The initial estimation of the parameter values could be achieved in any one of a number of ways, and may include for example using a look-up table which stores estimated parameter values for given ranges of impedance measurements. Thus, for example, the look-up table could indicate for a given measurement frequency, a number of different ranges of measured impedance values, with a respective set of estimated values being assigned for each range.

Alternatively, an operator may provide the initial parameter value estimates, or alternatively, pre-set initial estimate values may be used, depending on the preferred implementation.

Figure 8A:
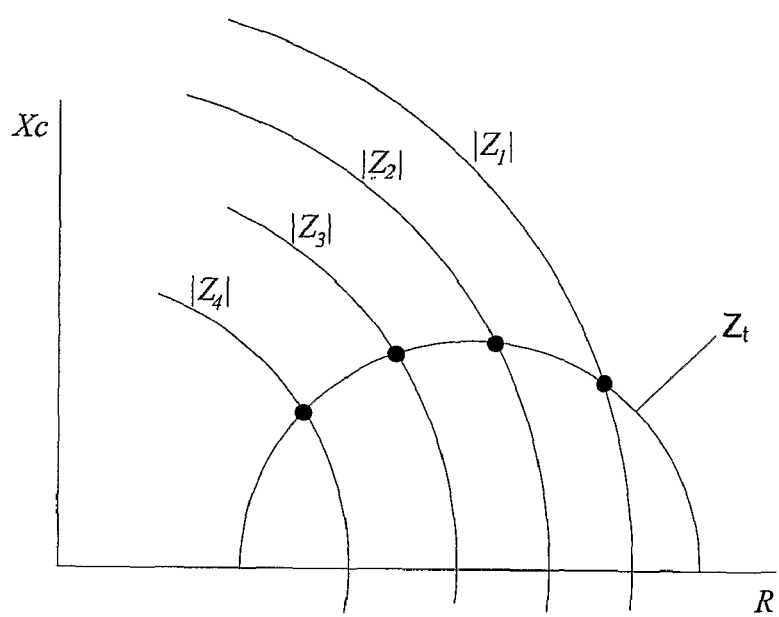
FIG. 8A is an example of the intersection of loci of measured impedance against and a theoretical impedance locus.
Figure 8B:
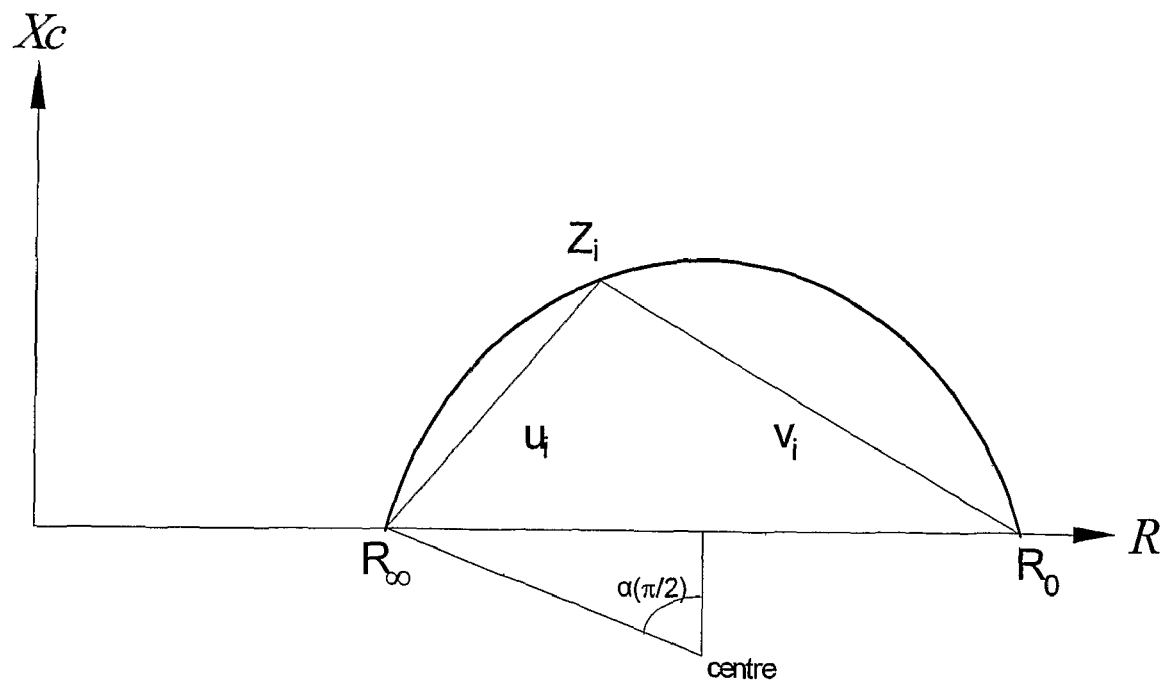
FIG. 8B is an example of the chords defined by the intersection of locus of measured impedance against a loci of theoretical locus; and, FIG. 8C is an example of a plot to determine a regression line.
Figure 8C:
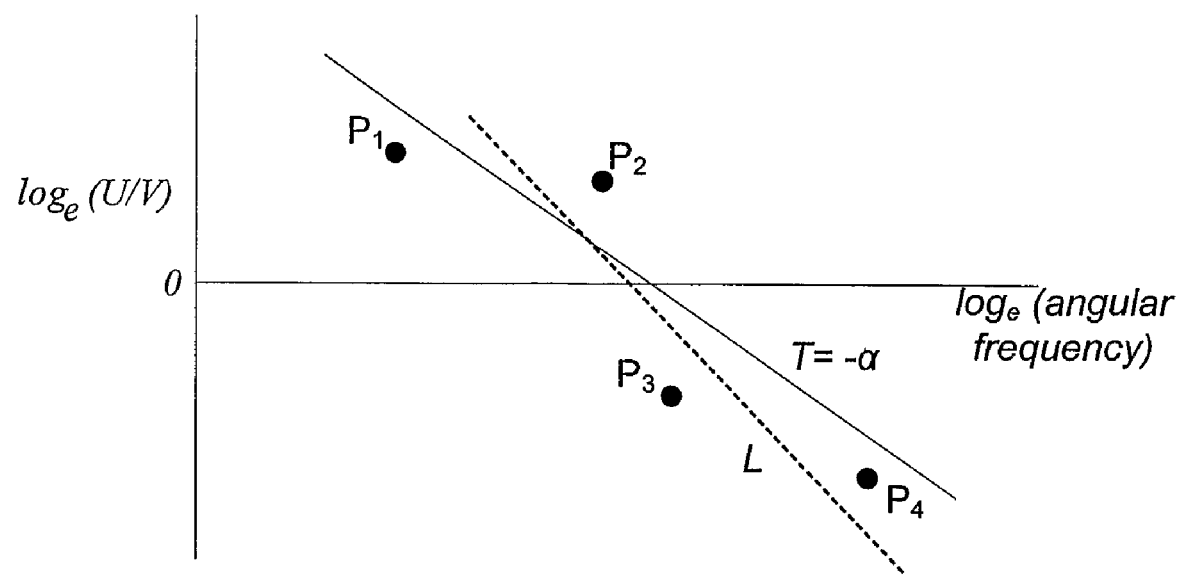

It should be noted that the theoretical impedance locus can be calculated without requiring a value for the parameter $\tau$ on the basis that the impedance locus is a semi-circle arranged as shown in FIG. 8B. Thus, given values for the parameters $R_0$, $R_\infty$ and $\alpha$, then a value for $\tau$ can be derived using known properties of equation (2) above.

Given that the above described process determines values for four unknown variables, namely $R_0$, $R_\infty$, $\alpha$, and $\tau$, it is necessary to use at least four measured impedance values in order to determine a unique solution. In this case, as the value r can be derived from the estimated values of $R_0$, $R_\infty$, $\alpha$, the value of $\tau$ can be used to assess the accuracy of the estimates for $R_0$, $R_\infty$, $\alpha$.

In this regard, the value of $\tau$ is related to the characteristic frequency (the frequency of maximum impedance response) by $f_c = 1/2\pi\tau$. Accordingly, once values of $R_0$, $R_\infty$ and $\alpha$, have been determined, a separate value could be determined for the characteristic frequency and hence $\tau$ from each measured impedance value. If the parameter values for $R_0$, $R_\infty$ and $\alpha$, are correct, the values of the characteristic frequency calculated for each measured impedance signal would be the same, thereby allowing the estimated values to be checked. In practice, this is achieved by creating a plot as will now be described.

In particular, the intersection of each impedance locus $Z_i$ with the theoretical impedance locus $Z_t$ is determined at step 230. An example of this is shown in FIG. 8A in which a locus for each of the four measured impedance values $Z_1, Z_2, Z_3, Z_4$ is shown to intersect with the theoretical impedance locus $Z_t$. At step 240, this is used to determine chord lengths $U_i, V_i$ for each intersection. An example of how the chord lengths $U_i, V_i$ are determined is shown in FIG. 8B.

It will be appreciated by persons skilled in the art that whilst steps 220 to 240 could be achieved by generating a physical plot of the measured and theoretical impedance loci $Z_i, Z_t$, this is not essential. Thus, for example, suitable calculations can alternatively be performed to determine the theoretical coordinates of the intersections.

At step 250, a chord length ratio $U_i/V_i$ is determined for each intersection, with this being used to plot corresponding points $P_1, P_2, P_3, P_4$ by plotting $\log_e(U_i/V_i), \log_e(\omega_i)$, for each of the intersections, at step 260. At step 270 the processing system 2 performs a linear regression utilising the points $P_1$, $P_2, P_3, P_4$ to determine a regression line L shown in FIG. 8C.

Whist a regression line L is used in this example, the process could operate using any line extending between $P_1$ and $P_4$ as the technique examines the gradient of the line and then modifies this until it fits with observed values. However, the use of a regression line ensures that the initial fit is as accurate as possible, thereby reducing computational requirements.

The processing system 2 can then use the regression line to improve the estimated values of $R_0$, $R_\infty$ and $\alpha$. This can be achieved taking into account that:

The position of point $P_2$ above or below the regression line is sensitive mainly to changes in $R_0$, and can therefore be used as feedback for $R_0$ estimation.

The position of point $P_3$ above or below the regression line is sensitive mainly to changes in $R_\infty$, and can therefore be used as feedback for $R_\infty$ estimation.

The slope of the regression line L can be compared with a target slope T defined as $(\alpha-1)$, and can therefore be use to provide feedback for $\alpha$ estimation.

In this regard, the value of points $P_2$ and $P_3$ are used for estimation of $R_0$ and $R_\infty$ respectively as the points are based on the impedance measurements near to $R_0$ and $R_\infty$, and therefore have a greater influence on these values.

At step 280 the processing system 2 determines the relative position of the point $P_2$ relative to the regression line L and determines if the point $P_2$ lies on the regression line L at step 290.

In this regard, the assessment will typically not be absolute, and will take into account a required precision for the resulting values of $R_0$, $R_\infty$. Thus, the assessment will typically determine if the point $P_2$ is within a predetermined distance from the regression line L.

If not, the processing system 2 operates to revise the value of $R_0$ and recalculates the regression line at step 300. The revision of $R_0$ is performed so that whether the value of $R_0$ is increased or decreased depends on the relative position of the point $P_2$ to the regression line L. Thus, for example, if $P_2$ is above the line then $R_0$ is decreased in value. This ensures that the modification of the estimated value of $R_0$ will always result in an improved estimate, thereby reducing the mathematical requirements for calculating suitable estimates.

The recalculation of the regression line L is performed using the general method set out in steps 210 to 270 and this will not therefore be described in detail.

If the point $P_2$ lies on the regression line L, or once the regression line has been revised at step 300, the processing system 2 determines the position of the point $P_3$ relative to the regression line L at step 310. Again if it is determined that the point $P_3$ does not lie on, or is not within a predetermined distance of, the regression line L at step 320, this is used to revise the value or R, and recalculate the regression line at step 330. In this case, if $P_3$ is above the line then $R_\infty$ is decreased in value. Again this is achieved using the steps by repeating the steps 210 to 270.

Once this has been completed, the processing system 2 assesses whether all four points $P_1, P_2, P_3, P_4$ lie on, or within a predetermined distance of the regression line L, at step 340. If this is not the case, the processing system 2 will return to step 280 to determine the position of point $P_2$ and repeat the steps 280 to 340.

Once all four points lie on, or within a predetermined distance of the regression line L, the process moves on to step 350 allowing the processing system 2 to compare the gradient of the regression line L to the gradient of the target slope T, which is given by $\alpha-1$.

If it is assessed that the gradients are not equal, or within a predetermined range, at step 360, the processing system 2 revises the value of a and returns to step 280 to recalculate the regression line L, and again assess the relative position of the points $P_2$, $P_3$ and the regression line L.

Once values for the estimates of $R_0$, $R_\infty$ and $\alpha$ are finalised, the points $P_1$, $P_2$, $P_3$, $P_4$ should lie on a straight line with a slope of $\alpha-1$, with $\log(U/V)$ being zero at the characteristic frequency $f_c=1/2\pi\tau$.

Thus, by using the estimated values to determine a common regression line L, this effectively tests the accuracy of the estimates for $R_0$, $R_\infty$ and $\alpha$.

At step 380 the processing system 2 determines at least the values of $R_0$ and $R_\infty$, and can optionally also determine the value $\tau$. These values can then be used in assessing the subject.

This can be achieved in a number of manners depending on the particular aspect of the patient being monitored.

For example, in assessing the presence, absence or degree of tissue oedema, it is typical to use the parameters to determine an index I based on a ratio of extra- to intra-cellular fluid, given by the equation:

$$I = \frac{R_i}{R_e} = \frac{R_\infty}{R_0 - R_\infty} \quad (3)$$

This is typically achieved by comparing the index I to a predetermined reference or range, which may be derived for example from:
- study of a reference population;
- comparison to an index previously determined for the subject, known as a longitudinal analysis; and,
- an index obtained from one or more other body segments for the individual.

Thus, the parameter values derived using the above techniques may be used in studying body composition, oedema detection, monitoring cardiac function, or the like.

In any event, the above-described process operates by estimating parameter values that can be used to model the impedance. The theoretical impedance values predicted by the model are compared to the measured values, allowing the estimated parameter values to be revised. In this regard, the comparison is performed in such a manner as to determine the direction in which the estimated parameter values should be revised, thereby vastly reducing the processing required to achieve acceptable parameter values.

Thus, this should be contrasted with other iterative techniques, such as method of least squares approaches, which only assess the magnitude of differences between calculated and measured values. In such approaches, assessment of magnitude only means that modification of the estimated values can result in worse estimates, thereby increasing the processing required to achieve a satisfactory estimate. Furthermore, because, the process effectively adjusts each of four parameter values corresponding to $R_0$, $R_\infty$, $\tau$ and $\alpha$, and uses this to "explore" an error surface, there is a risk that the process will locate a local minimum value that does not necessarily corresponding to the best parameter combination.

In contrast, the above process derives feedback for controlling the adjustment direction of three estimated parameter values $R_0$, $R_\infty$, and $\alpha$, with the value of the fourth parameter value $\tau$ being used to ensure the estimated values are correct. Thus, as direction of modification of the estimated values is determined, this vastly reduces processing requirements, making the process suitable for determining the values $R_0$, $R_\infty$, in real-time.

In the above described example, the processing of the measured impedance values is described as being performed by the processing system 2. In this regard, it will be appreciated that the process may be performed entirely by either one of the first or second processing systems 10, 17, or a combination or the two.

Additionally, or alternatively, any one or more of processing tasks may be performed by a remote processing system, such as a computer system or the like, coupled to the measuring device via the external interface 23. In this arrangement, the remote processing system therefore effectively forms part or all of the processing system 2. Accordingly, this allows the measuring device 1 to perform the impedance measurement procedure and provide the resulting impedance measurements to the remote processing system, to allow the impedance parameter values to be calculated using the above described process. Alternatively, calculation may be performed entirely within the measuring device.

In any event, it will be appreciated that in one example, a remote processing system may perform tasks otherwise performed by the first processing system 10, allowing the measuring device 1 to be provided including only the second processing system 17 coupled directly to the external interface 23. This allows the measuring device 1 to be controlled by the remote processing system. This would typically be achieved via the use of suitable applications software installed on the remote processing system.

In another example, the above described process may be used with an alternative measuring devices, including implantable devices such as cardiac pacemakers or defibrillators. In particular, in the case of implantable devices, it is typical to minimise both the power consumption and physical size of the device, to make the device practical for use. As a result, implantable devices typically have only limited processing ability, and are not generally able to measure the phase of signals at more than one frequency.

Accordingly, the above described process could be used to estimate various cardiac parameters such as oedema or heart function by measuring the magnitude of impedance only at several frequencies. This approach would enable the estimation of multifrequency results for low power small implantable devices.

The discussion has referred to both oedema and lymphoedema, as it is clear to a skilled addressee that the above method and apparatus may be utilised on any form of impedance measurements including, but not limited to body composition, cardiac function, tissue oedema, pulmonary oedema, or the like. The method may also be used to derive indices that can be compared to references, such as previously determined indices, indices derived from different anatomical region or different individuals, thereby allowing different forms of analysis to be performed, depending on the circumstances in which the process is used.

Throughout the specification, the aim has been to describe the preferred embodiments of the invention without limiting the invention to any one embodiment or specific collection of features. Various changes and modifications may be made to the embodiments described and illustrated without departing from the present invention.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such as race horses, or the like.

The above described processes can be used for diagnosing the presence, absence or degree of a range of conditions and illnesses, including, but not limited to oedema, lymphodema, body composition, cardiac function, or the like.

The claims defining the invention are as follows:

1. A method of determining parameter values used in impedance analysis of a subject, the method comprising:
   a) determining a number of impedance measurements at a corresponding number of frequencies;
   b) determining estimates of the parameter values;
   c) determining theoretical impedance values based on the parameter value estimates;
   d) comparing, in a processor of a processing system, the theoretical impedance values to the measured impedance values;
   e) determining, in the processor, at least one modification direction for at least one of the parameter value estimates in accordance with the results of the comparison; and,
   f) modifying, in the processor, at least one parameter value estimate in accordance with the determined direction, the parameter values being determined at least in part from one or more modified parameter value estimates.

2. A method according to claim 1, wherein the method includes, in the processing system, iteratively modifying the parameter value estimates to thereby determine the parameter values.

3. A method according to claim 1, wherein the method includes, in the processing system, comparing the theoretical impedance values to the measured impedance values:
   a) determining a theoretical impedance locus using the parameter value estimates;
   b) determining a measured impedance locus associated with each measured impedance; and,
   c) determining an intersection between each measured impedance locus and the theoretical impedance locus.

4. A method according to claim 3, wherein the method includes, in the processing system:
   a) determining a point associated with each intersection;
   b) determining a linear regression based at least partially on the points; and,
   c) determining the modification direction based at least partially on at least one of:
      i) the relative position of the regression line and at least one of the points; and,
      ii) the gradient of the regression line.

5. A method according to claim 4, wherein the method includes, in the processing system:
   a) determining a pair of chords associated with each point of intersection, the chords representing the distance to locations at which the theoretical impedance locus represents predetermined impedance values; and,
   b) determining a point associated with each pair of chords; and,
   c) determining the linear regression in accordance with the value of the points.

6. A method according to claim 1, wherein the method includes, in the processing system:
   a) determining four impedance measurements, each impedance measurement being made at a respective frequency;
   b) comparing each measured impedance value to a corresponding theoretical impedance value;
   c) determining the modification direction based at least in part on the results of the comparison.

7. A method according to claim 6, wherein the method includes, in the processing system:
   a) determining a point based on the comparison of each measured impedance value with a corresponding theoretical impedance value;
   b) determining a linear regression based at least partially on the points; and,
   c) determining the modification direction based at least partially on at least one of:
      i) the relative position of the regression line and at least one of the points; and,
      ii) the gradient of the regression line.

8. A method according to claim 7, wherein the method includes, in the processing system:
   a) determining the relative position of the regression line and a predetermined point; and,
   b) determining the modification direction for modifying a predetermined one of the parameter value estimates using the relative position.

9. A method according to claim 7, wherein the method based on the relative position of the regression line and at least one of the points.
   a) comparing the gradient of the regression line and a line based on at least one of the parameter value estimates; and,
   b) determining the modification direction for the at least one of the parameter value estimate using the results of the comparison.

10. A method according to claim 7, wherein the method includes, in the processing system, at least one of:
    a) modifying an estimated value of $R_0$ using a point based on the impedance measured at a first frequency;
    b) modifying an estimated value of $R_\infty$ using a point based on the impedance measured at a second frequency; and,
    c) modifying an estimated value of a using αgradient of the regression line, where: αhas a value between 0 and 1; $R_0$ is the theoretical impedance at zero applied angular frequency; and, $R_\infty$ is the theoretical impedance at infinite applied angular frequency.

11. A method according to claim 1, wherein the method includes, in the processing system, estimating values for parameters $R_0$, $R_\infty$, and α, where: α has a value between 0 and 1; $R_0$ is the theoretical impedance at zero applied angular frequency; and, $R_\infty$ is the theoretical impedance at infinite applied angular frequency.

12. A method according to claim 1, wherein the method includes, in the processing system, determining the theoretical impedance using the equation:

$$Z = R_\infty + \frac{R_0 - R_\infty}{1 + (j\omega\tau)^\alpha} \text{ where:}$$

Z is the measured impedance at angular frequency ω,
$R_0$ is the resistance at zero frequency,
$R_\infty$ is the resistance at infinite frequency,
τ is a time constant, and
αhas a value between 0 and 1.

13. A method according to claim 1, wherein the method includes, in the processing system, using the parameter values to determine at least one of:
    a) a ratio of extra- to intra-cellular fluid; and,
    b) an indication of the at least one of the presence, absence or degree of tissue oedema in the subject.

14. A method according to claim 1, wherein the includes, in the processing system:
    a) determining parameter values associated with first and second body segments;
    b) for each body segment, determining an index indicative of a ratio of the extra- to intra-cellular fluid;

c) determining an index ratio based on the index for the first and second body segments;
d) comparing the index ratio to at least one reference; and,
e) determining the presence, absence or degree of tissue oedema based on the results of the comparison.

15. A method according to claim 13, wherein the method includes, in the processing system, displaying an indication of at least one of:
a) the parameter values;
b) a ratio of extra- to intra-cellular fluid; and,
c) an indication of the at least one of the presence, absence or degree of tissue oedema in the subject.

16. A method according to claim 1, wherein the method includes, in the processing system, receiving the impedance measurements from a measuring device.

17. A method according to claim 1, wherein the method includes, in the processing system:
a) causing one or more electrical signals to be applied to the subject using a first set of electrodes, the one or more electrical signals having a plurality of frequencies;
b) determining an indication of electrical signals measured across a second set of electrodes applied to the subject in response to the applied one or more signals;
c) determining from the indication and the one or more applied signals, an instantaneous impedance value at each of the plurality of frequencies; and,
d) determining the index using the instantaneous impedance values.

18. A method according to claim 1, wherein the method includes, in the processing system:
a) generating control signals, the control signals being used to apply one or more signals to the subject;
b) receiving an indication of the one or more signals applied to the subject;
c) receiving an indication of one or more signals measured across the subject; and,
d) determining the impedance measurements using the received indications.

19. Apparatus for determining parameter values used in impedance analysis of a subject, the apparatus including a processing system for:
a) determining a number of impedance measurements at a corresponding number of frequencies;
b) determining estimates of the parameter values;
c) determining theoretical impedance values based on the parameter value estimates;
d) comparing, with a processor of the processing system, the theoretical impedance values to the measured impedance values;
e) determining, with the processor, at least one modification direction for at least one of the parameter value estimates in accordance with the results of the comparison; and,
f) modifying, with the processor, the at least one parameter value estimate in accordance with the determined direction.

20. Apparatus according to claim 19, wherein the apparatus includes:
a) a current supply for generating an alternating current at each of the number of frequencies;
b) at least two supply electrodes for applying the generated alternating current to a subject;
c) at least two measurement electrodes for detecting a voltage across the subject; and,
d) a sensor coupled to the measurement electrodes for determining the voltage, the sensor being coupled to the processing system to thereby allow the processing system to determine the measured impedance.

21. Apparatus according to claim 20, wherein the current supply generates the alternating current at each frequency by at least one of:
a) superposing a number of signals to thereby generate an alternating current at each frequency simultaneously; and,
b) generating a number of alternating currents, each alternating current being at a respective frequency, in turn.

22. A method of diagnosing the presence, absence or degree of one or more conditions in a subject, the method comprising:
a) determining a number of impedance measurements at a corresponding number of frequencies;
b) determining estimates of the parameter values;
c) determining theoretical impedance values based on the parameter value estimates;
d) comparing, in a processor of a processing system, the theoretical impedance values to the measured impedance values;
e) determining, in said processor, at least one modification direction for at least one of the parameter value estimates in accordance with the results of the comparison;
f) modifying, using said processor, at least one parameter value estimate in accordance with the determined direction, the parameter values being determined at least in part from one or more modified parameter value estimates; and,
g) using the determined parameter values in diagnosing the presence, absence or degree of one or more conditions in the subject.

23. An apparatus for determining parameter values used in impedance analysis of a subject, the apparatus comprising:
a) means for determining a number of impedance measurements at a corresponding number of frequencies;
b) means for determining estimates of the parameter values;
c) means for determining theoretical impedance values based on the parameter value estimates;
d) means for comparing the theoretical impedance values to the measured impedance values;
e) means for determining at least one modification direction for at least one of the parameter value estimates in accordance with the results of the comparison; and,
f) means for modifying at least one parameter value estimate in accordance with the determined direction, the parameter values being determined at least in part from one or more modified parameter value estimates.

24. The method of claim 1, wherein determining a number of impedance measurements at a corresponding number of frequencies comprises:
obtaining a number of electrical signals measured across a set of electrodes applied to a subject; and
determining a number of impedance measurements at a corresponding number of frequencies using said electrical signals.

25. The method of claim 24, wherein the processing system is situated remote to said subject.

26. A method of determining parameter values used in impedance analysis of a subject, the method including, in a processing system:
determining an indication of electrical signals measured across a set of electrodes applied to the subject;
determining, using said indication, a number of impedance measurements at a corresponding number of frequencies;

determining estimates of the parameter values;
determining theoretical impedance values based on the parameter value estimates;
comparing the theoretical impedance values to the measured impedance values;
determining at least one modification direction for at least one of the parameter value estimates in accordance with the results of the comparison; and, modifying at least one parameter value estimate in accordance with the determined direction, the parameter values being determined at least in part from one or more modified parameter value estimates.

27. The method of claim 26, wherein the processing system is situated remote to the subject.

* * * * *